US005997842A

United States Patent [19]
Chen

[11] Patent Number: 5,997,842
[45] Date of Patent: Dec. 7, 1999

[54] RADIONUCLIDE EXCITED PHOSPHORESCENT MATERIAL FOR ADMINISTERING PDT

[75] Inventor: James C. Chen, Bellevue, Wash.

[73] Assignee: Light Sciences Limited Partnership, Issaquah, Wash.

[21] Appl. No.: 09/059,795

[22] Filed: Apr. 13, 1998

[51] Int. Cl.⁶ .......................... A61K 51/00; A61M 36/14
[52] U.S. Cl. .......................... 424/1.29; 424/9.1; 424/9.6; 424/1.11; 604/19; 604/20
[58] Field of Search .................................. 424/1.11, 1.49, 424/1.65, 1.61, 1.77, 1.81, 9.1, 9.3, 9.4, 9.5, 1.29, 9.6, 422, 450; 604/19, 20

[56] References Cited

U.S. PATENT DOCUMENTS 5,445,608   8/1995   Chen et al. ................................ 604/20

FOREIGN PATENT DOCUMENTS

98/06456   2/1998   WIPO .

OTHER PUBLICATIONS

Deborah Kotz, "Alpha Particle Therapy Poised to Become New Line of Cancer Treatment," The Journal of Nuclear Medicine, Newsline, vol. 39, No. 2, Feb. 1998, pp. 17N–19N and 36N (4pp).

Kate Leggett, "Dosimeter helps monitor prostate cancer treatment," Biophotonics International, Jan.–Feb., 1998, p. 28.

Greg T. Hermanson, "Modification with Synthetic Polymers," Bioconjugate Techniques, Chapter 15, Academic Press, Division of Harcourt Brace & Company, © 1996 by Academic Press, Inc., pp. 605–629.

Boris M. Krasovitskii, "Organic Scintillators," Organic Luminescent Materials, Chapter 12, © 1988 by VCH Verlagsgesellschaft mbH, Germany, Library of Congress Card No. 88–20895, pp. 200–210.

Mitsuru Akashi, "Polymers for Pharmaceutical and Biomolecular Engineering," Biomedical Applications of Polymeric Materials, Chapter 6 (Teiji Tsuruta et al., Eds.), © 1993 by CRC Press, Inc., pp. 371–406.

S.S. Davis and L. Illum, "Particulate Systems for Site Specific Drug Delivery," Targeting of Drugs 4 (G. Gregoriadis et al. Eds.), Plenum Press, New York, 1994, pp. 183–194.

Haruma Kawaguchi, "Polymer Materials for Bioanalysis and Bioseparation," Biomedical Applications of Polymeric Materials, Chapter 5 (Teiji Tsuruta et al., Eds.), © 1993 CRC Press, Inc., pp. 299–324.

Brenda McCormack and Gregory Gregoriadis, "Polysialic Acids: In Vivo Properties and Possible Uses in Drug Delivery," Targeting of Drugs 4 (G. Gregoriadis et al. Eds.), Plenum Press, New York, 1994, pp. 139–145.

Prof. Dr. G. Blasse and Prof. Dr. B.C. Grabmaier, "X–Ray Phosphors and Scintillators (Counting Techniques)," Luminescent Materials, Chapter 9, © Springer Verlag Berlin Heidelberg, 1994, pp. 170–194.

Lewis (1993), Hawley's Twelveth Edition Condensed Chemical Dictionary, pp. 142, 907 & 908.

Primary Examiner—Jose' G. Dees
Assistant Examiner—Dameron Jones
Attorney, Agent, or Firm—Ronald M. Anderson

[57] ABSTRACT

Constructs including bars, capsules, beads, and sheets are configured with a radionuclide core that emits energetic particles activating a phosphorescent shell material surrounding the radionuclide core so that it emits light to administer light therapy or PDT. A biocompatible coating that is generally optically transparent encloses the radionuclide core and phosphorescent material to prevent a patient's body in which the constructs are disposed from being affected by any toxicity of the phosphorescent shell material. In a typical application of the constructs, a photoreactive agent is infused into the treatment site and selectively absorbed by abnormal tissue, for example, in a cancerous tumor. Light emitted by the phosphorescent material when activated by the energetic particles emitted from the radionuclide core administers photodynamic therapy, which destroys the abnormal tissue. Particularly, the beads, which are relatively small in size, can be targeted to abnormal tissue by providing a linking mechanism on the biocompatible coating so that the beads are coupled to antibodies found on the abnormal cells, but not on normal tissue. If a glass phosphor material that includes fused quartz or silica glass doped with metal ions is used for the phosphorescent shell material, the beads or other construct must be exposed to IR or other light, causing electrons that have been trapped inside the glass materials to combine with holes, emitting light of a shorter wavelength. The glass phosphor material is preferable, since it is substantially less toxic than other types of scintillators or phosphor materials.

38 Claims, 7 Drawing Sheets

RADIONUCLIDE EXCITED PHOSPHORESCENT MATERIAL FOR ADMINISTERING PDT

FIELD OF THE INVENTION

The present invention generally pertains to the excitation of a phosphorescent substance by particles emitted from an appropriate particle emitting source, and more specifically, to the emission of photons from the phosphorescent substance that is disposed proximate a radionuclide particle emitter, which is implanted within a patient's body.

BACKGROUND OF THE INVENTION

Photodynamic therapy (PDT) is commonly administered to a treatment site that is disposed on or within a patient's body using a light source that is energized with an electrical current. The light source, which may be positioned either external or internal to the patient's body, emits light having a characteristic wave band selected to match an absorption wave band of a photodynamic reagent that has been administered to the treatment site. The photoreactive reagent is preferentially absorbed by abnormal tissue at the treatment site. When exposed to the light, the abnormal tissue that has absorbed the photoreactive agent is destroyed.

U.S. Pat. No. 5,445,608 (Chen et al.) discloses that even relatively low intensity light, such as that produced by light emitting diodes (LEDs), can be very effective in destroying abnormal tissue and undesired organisms within a patient's body. Because of the relatively low intensity of the light emitted by an LED compared to a high power laser, the treatment is preferably administered for an extended period of time, or at least for a longer time than would be done if a high intensity laser light source were used as the light source. This patent reference also discloses several embodiments for probes that includes such low intensity light sources and which are intended to be implanted within a patient's body to administer PDT for relatively longer periods of time, thereby destroying a tumor or abnormal cells at an internal treatment site. However, electrical power must be supplied to energize the light sources on the implanted probe. The patent teaches that either a battery and/or an internal power supply receiving energy from an external power source, e.g., by electromagnetically coupling the internal power supply to the external power source, can be used for energizing the light sources on the probe.

Clearly, there would be significant advantages in developing a system for delivering light therapy that does not include a battery, does not require recharging, and which does not require any energy transfer from outside the patient's body. Instead, such a system would be self-powered to obviate the need for continual or intermittent power transfer from an external power source. By eliminating a battery supply and/or a power receiver coil, a system for administering PDT could be substantially simplified, requiring fewer components, and could be greatly reduced in size. This reduction in size might facilitate the administration of PDT to an internal treatment site not readily achieved with larger and more complex devices that must be intermittently coupled to an external power source or which must include a relatively large power storage device.

It would also be desirable to enable a light source disposed within a patient's body to be easily moved to a treatment site and maintained at that position. Further, once the light therapy has been completed, it would be desirable to enable the light source to be readily removed from the patient's body, preferably without the need for invasive surgery. The self-energized light source should also preferably be sealed to minimize any risk of exposure of the patient to components of the system used to administer the therapy that might be toxic and to protect the light delivery system from damage due to exposure to bodily fluids.

SUMMARY OF THE INVENTION

In accord with the present invention, a construct is defined for administering a light therapy to an internal treatment site within a patient's body. The construct includes a source of energetic nuclear particles; also included is a substance that absorbs the energetic nuclear particles, and in response thereto, emits light having a characteristic wave band. This substance is preferably disposed proximate to the source of energetic nuclear particles to ensure that the particles are absorbed, causing the light to be emitted by the substance. A substantially optically transparent, biocompatible envelope surrounds the source of energetic nuclear particles and the substance, so that light emitted by the substance passes through the envelope to administer the light therapy to the treatment site.

The source of energetic nuclear particles preferably comprises a core that is at least partially surrounded by a shell of the substance that emits light. The envelope encloses the shell and the core to prevent direct contact between the patient's body and either the source of the energetic particles or the substance. In addition, the envelope preferably comprises a material that absorbs at least some of the energetic nuclear particles that are not absorbed by the substance. In at least one form of the invention, this envelope comprises a material that is adapted to molecularly bind to a cell at the treatment site, linking the envelope, the source of energetic particles, and the substance to the cell so that the light emitted by the substance is absorbed by the cell.

The construct may further comprise a magnetically attracted component, which adapts the construct to be magnetically attracted to the treatment site with a magnetic field. In addition, the magnetically attracted component may adapt the construct to be magnetically attracted to a removal site after the light therapy has been administered, thereby facilitating removal of the construct from the patient's body.

In one configuration of the invention, the source of the energetic nuclear particles is formed into a sheet having a thickness substantially less than either a width or a length of the sheet. In another configuration, the source of the energetic nuclear particles is formed into a generally elongate configuration.

The substance preferably comprises a phosphorescent compound having valence electrons that are excited to higher energy states by absorption of the energetic nuclear particles emitted from the source. These valence electrons then emit the light as they drop to lower energy states. For example, the phosphorescent compound may comprise a sulfide molecule. In a preferred form of the invention, the energetic nuclear particles comprise either alpha particles or beta particles.

The envelope is substantially spherical in one embodiment of the invention. Further, in at least one embodiment, the envelope preferably has a maximum dimension in a range between $10^{-4}$ mm and 10 mm, although it is expected that the invention will also be usable outside this range.

The source of energetic nuclear particles may emit gamma radiation to facilitate detection of the construct within a patient's body, thereby enabling the construct to be more easily located and removed after the light therapy has been administered.

To minimize a risk of exposing the patient's body to the energetic nuclear particles after the light therapy has been completed, the source of the energetic nuclear particles is preferably selected to have a specific half-life based upon an expected required duration of the light therapy. The source of the energetic particles preferably comprises one or more isotopes of elements selected from the group consisting of hydrogen, gold, phosphorus, radon, yttrium, bismuth, astatine, and strontium.

In one form of the invention, the construct is adapted to be suspended within a biologically compatible liquid for delivery to the treatment site.

Another aspect of the present invention is directed to a method for administering a light therapy to an internal treatment site within a patient's body. The method includes steps that are generally consistent with the functions provided by the elements of the construct discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1A:
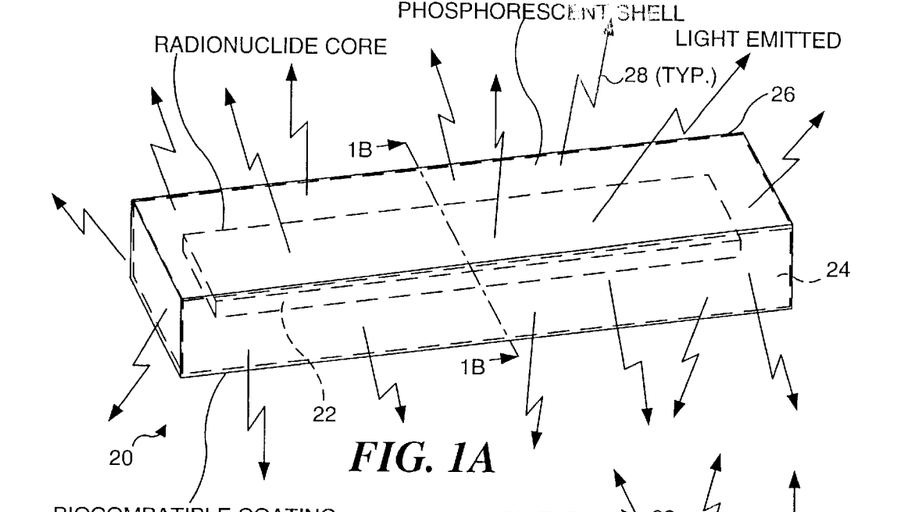
FIG. 1A is an isometric view of an elongate bar (greatly enlarged) constructed in accord with the present invention, where a radionuclide core is enclosed with a phosphorescent material and sealed with a biocompatible coating.
Figures 1B, 2A, 2B:
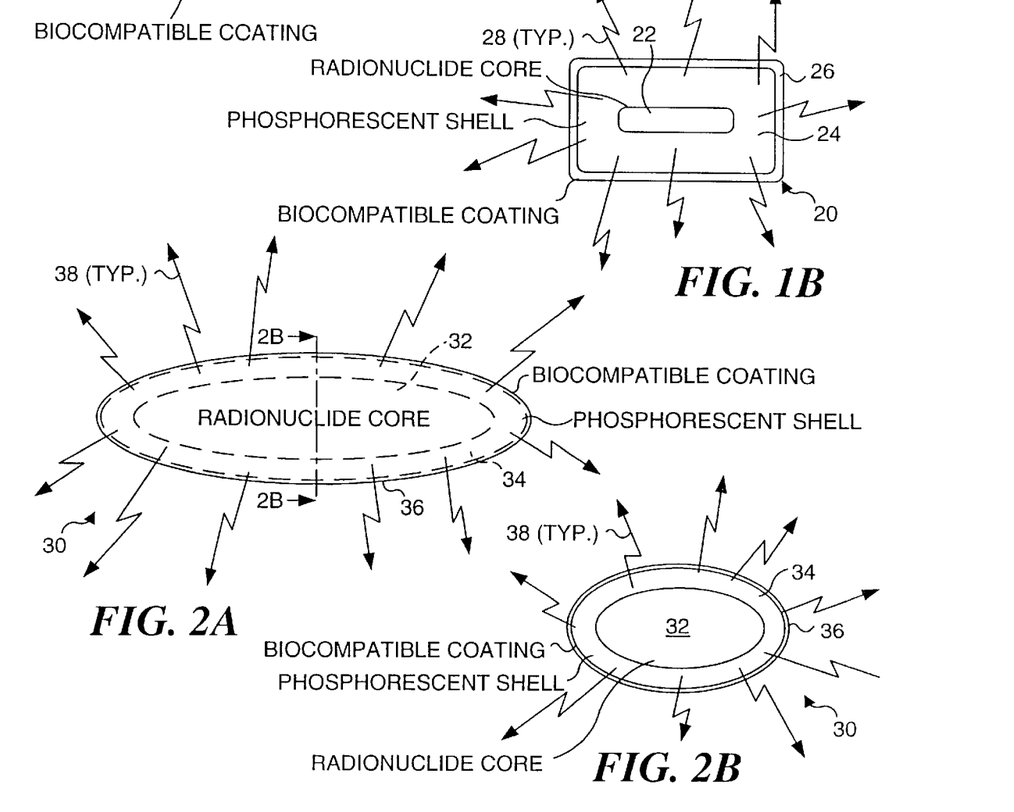
FIG. 1B is a cross-sectional view of the elongate bar taken along section lines 1B—1B in FIG. 1A.
FIG. 2A is a plan view of a generally oval-shaped embodiment of the present invention.
FIG. 2B is a cross-sectional view of the oval-shaped embodiment, taken along section lines 2B—2B in FIG. 2A.

Referring to FIGS. 1A and 1B, a first embodiment of the present invention is illustrated taking the form of an elongate bar 20. Bar 20 is illustrated enlarged compared to its typical actual size, since it is intended to be implanted within the body of the patient to which light therapy is to be administered by the bar. However, it is likely that the bar 20 will be several centimeters in length for certain applications of this invention. While the light therapy delivered by the present invention is preferably PDT, it is also expected that other types of light therapy could be administered with any of the embodiments of the present invention that are described herein.

Bar 20 is generally rectangular in shape when viewed in cross section as shown in FIG. 1B. Within the center of bar 20 is disposed an elongate and generally rectangular shaped radionuclide core 22, which serves as a source of low energy electrons, protons, alpha particles or beta particles. While the other types of emissions are useful in this application, alpha and beta particles are actually preferred because of their minimal effect on tissue within the patient's body due their limited penetration. Particularly, alpha particles have very little penetrating power, since they can be stopped by a single sheet of paper. Selection of the specific material used in fabricating bar 20 in each of the embodiments of the present invention typically depends upon the type of emissions produced by the material and its half life, as discussed below.

Surrounding radionuclide core 22 in bar 20 is a phosphorescent shell comprising an appropriate scintillator or phosphor that responds to the particular type of particles emitted by radionuclide core 22. The term "phosphorescent shell" is intended to encompass various types of phosphor materials or scintillators that are characterized by their ability to absorb particles emitted by the radionuclide core and in response thereto, to emit light that provides the PDT or other light therapy to a treatment site within a patient's body (not shown). For purposes of administering PDT, the light emitted by a phosphorescent shell 24 should lie within a wave band corresponding to an absorption wave band of a photoreactive agent that has previously been infused into the treatment site and preferentially absorbed by abnormal cells at that site. Upon absorbing light of the appropriate wave band that corresponds to the absorption wave band of the photoreactive agent, the tumor cells or other abnormal tissue that have absorbed the photoreactive agent are destroyed.

It will be apparent that if one or a plurality of bars 20 are implanted adjacent to a treatment site in which a tumor or other abnormal tissue is disposed, the light emitted by these devices will be effective to substantially destroy the abnormal tissue. Although the intensity of the light emitted by the phosphorescent shell may be relatively low compared to that used for conventional PDT in which a laser light source is employed, since the light is administered for an extended period of time, its efficacy in destroying abnormal tissue or undesired organisms should be quite high. Phosphorescent shell 24 and radionuclide core 22 are enclosed within a biocompatible coating 26 that is generally optically transparent so that the light emitted by phosphorescent shell 24 passes freely through the biocompatible coating to reach the abnormal tissue at the treatment site. Biocompatible coating 26 preferably comprises a polymer selected for its biocompatibility so that the patient's body is not exposed to the potentially toxic material comprising phosphorescent shell 24. In addition, the biocompatible coating serves to absorb alpha particles or other energetic particles emitted by radionuclide core 22 that have passed through phosphorescent shell 24 without interacting with the material comprising the shell. In each of the embodiments of the present invention that are disclosed herein, corresponding functions are carried out by the biocompatible coatings for the embodiments.

A second embodiment of the present invention is illustrated in FIGS. 2A and 2B and is in the form of a capsule 30. Capsule 30 includes a radionuclide core 32, a phosphorescent shell 34, and is enclosed in a biocompatible coating 36. Just as noted in regard to bar 20, capsule 30 is greatly enlarged compared to its actual size. It is contemplated that the maximum dimension for the disclosed embodiments of this invention will fall within the range of $10^{-4}$ mm to 10 mm. Capsule 30 is also intended to be introduced into a patient's body and positioned at a treatment site to apply light therapy to tissue at that location. The function and composition of the radionuclide core, phosphorescent shell, and biocompatible coating of this and each of the other embodiments discussed below are generally identical to that disclosed in connection with the embodiment of FIGS. 1A and 1B, except where indicated.

Figure 3A:
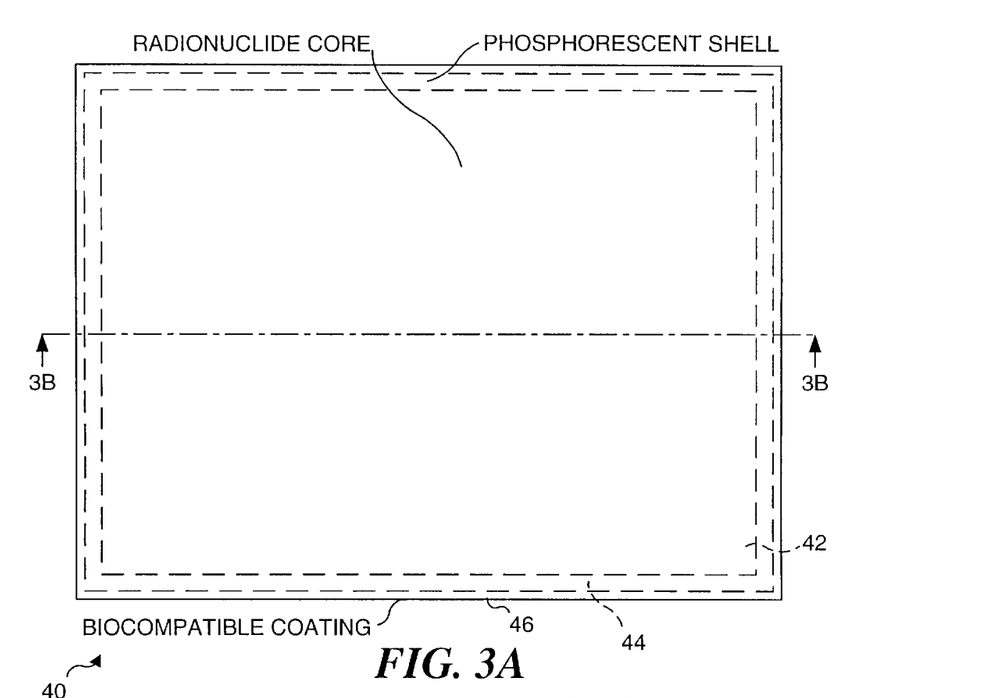
FIG. 3A is a plan view of a sheet-shaped embodiment of the present invention.
Figure 3B:
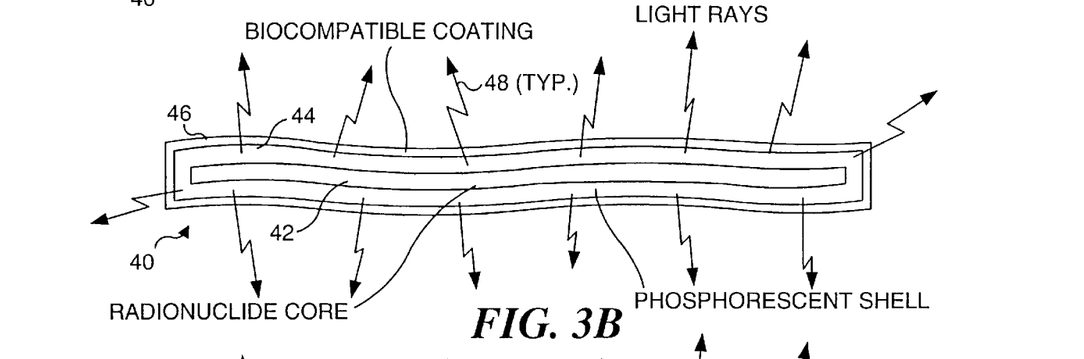
FIG. 3B is a cross-sectional view of the sheet-shaped embodiment, taken along section lines 3B—3B in FIG. 3A.
Figure 3C:
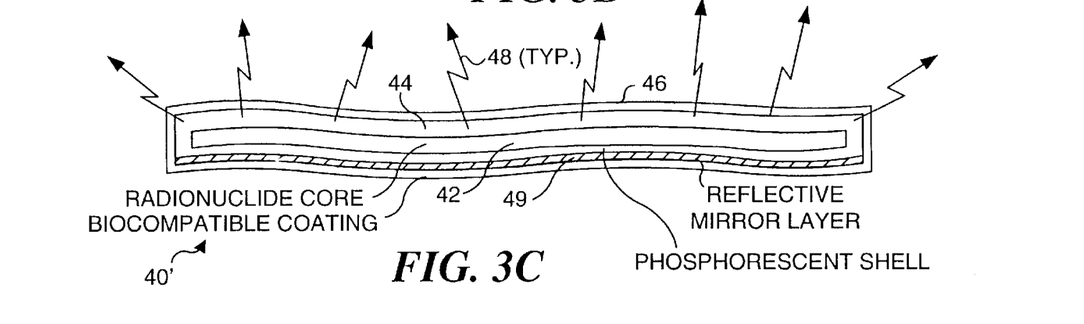
FIG. 3C is a cross-sectional view of a modified form of the sheet-shaped embodiment, corresponding to the view shown in FIG. 3B.

Bars 20 and capsules 30 are most likely to be used in plural form for rendering light therapy. In contrast, a sheet 40 is disclosed in FIGS. 3A–3C as yet another embodiment of the present invention, which may be used in singular form to provide light therapy. Sheet 40 includes a radionuclide core 42, a phosphorescent shell 44, and a biocompatible coating 46 completely enclosing the radionuclide core and phosphorescent shell. Although shown as a rectangular sheet in FIG. 3A, it is also contemplated that other shapes (in plan view) could be employed for sheet 40. Sheet 40 is sufficiently flexible so that it can be folded around a non-planar treatment site, e.g., around the outer surface of an organ that is somewhat spherical in shape. As shown in FIG. 3B, phosphorescent shell 44 absorbs particles from the radionuclide core, emitting light 48 in all directions. An alternative sheet 40' is illustrated in FIG. 3C that includes a reflective mirror layer 49 covering one surface of phosphorescent shell 44. Reflective mirror 49 reflects light 48 emitted from the phosphorescent shell that is incident on the reflective mirror so that the light is transmitted through only one surface of sheet 40' rather than both surfaces. Thus, an advantage of sheet 40', compared to sheet 40, is the increased luminance along the one surface through which light 48 is transmitted, which would be directed toward the treatment site.

Figures 4A, 5A, 5B:
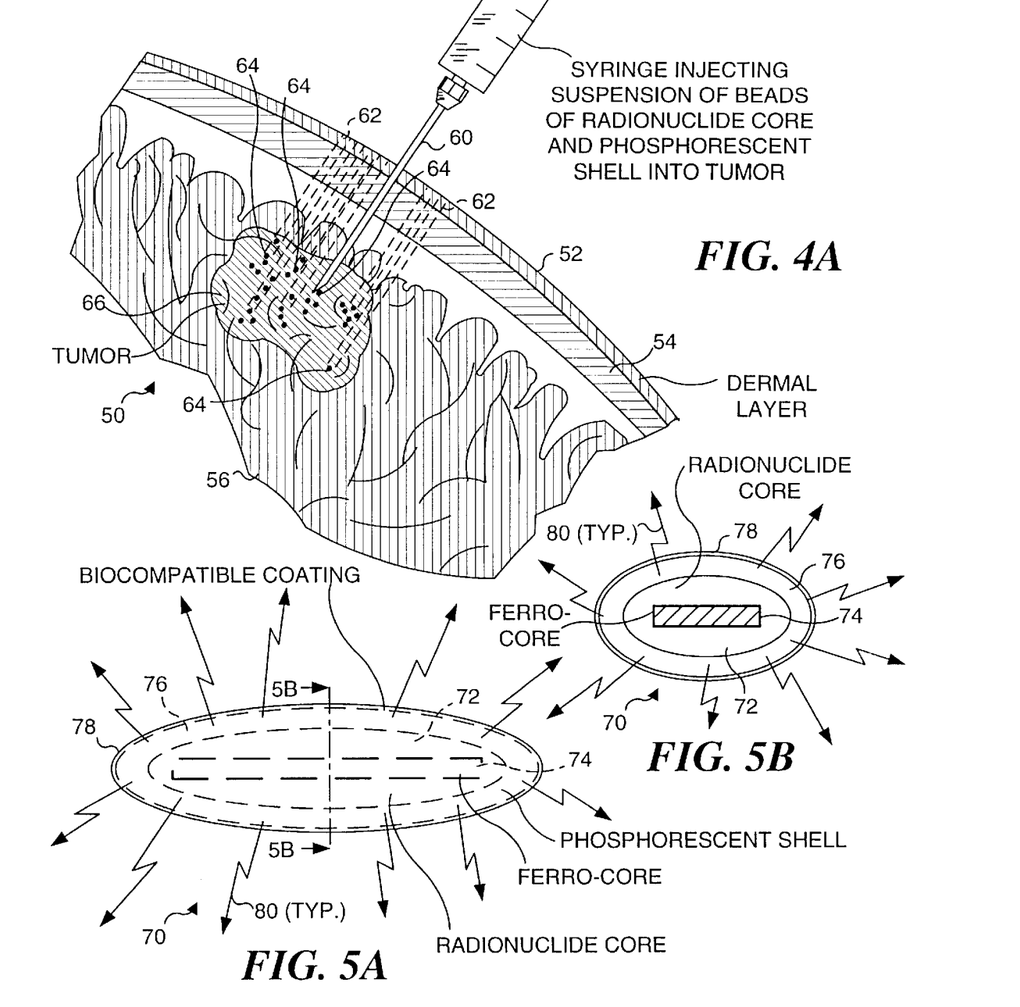
FIG. 4A is a cross-sectional view of a portion of a patient's body showing a syringe being used to inject a fluid containing beads comprising another embodiment of the present invention, into a tumor.
FIG. 5A is a plan view of yet another embodiment of the present invention that is oval shaped, but which includes a magnetically attracted core.
FIG. 5B is a cross-sectional view of the embodiment shown in FIG. 5A, taken along section lines 5B—5B.
Figure 4B:
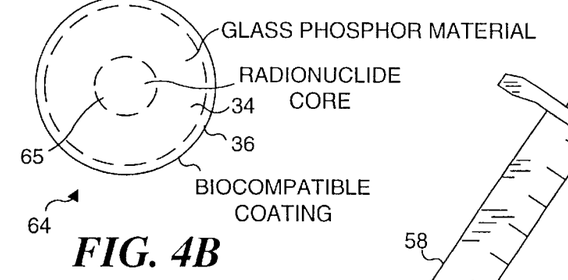
FIG. 4B is an elevational view of a bead-shaped embodiment of the present invention, which is usable as indicated in FIG. 4A.

FIG. 4B illustrates a bead 64 that comprises yet another embodiment of the present invention. Bead 64 includes a radionuclide core 65 that is surrounded by a glass phosphor material 34, which is yet another form of phosphorescent shell. A biocompatible coating 36 completely encloses glass phosphor material 34. In size, beads 64 are expected to be within the range of $10^{-3}$ to $10^{-4}$ mm. Glass phosphor material 34 is somewhat different than the phosphors or scintillators used in the previously described embodiments for the phosphorescent shell, since it comprises fused quartz or silica glass that has been doped with metal ions such as copper. Such doped glasses exhibit optical stimulated luminescence. When such glasses are subjected to ionizing radiation, electrons become trapped inside them. Thereafter, when subsequently illuminated with visible or IR light, the trapped electrons are released and combine with holes in the glass, resulting in emission by shorter wavelength light. Accordingly, to achieve light emission from bead 64 made with the glass phosphor material, an additional step is required. The radionuclide core provides the ionizing radiation necessary to trap electrons inside the glass phosphor material. However, it is necessary to illuminate the beads with IR light so that the beads will then emit light of a different wavelength in a wave band suitable for administering the light therapy or PDT to the treatment site. Beads 64 are most expediently infused into or adjacent to a treatment site when suspended in a biocompatible fluid, such as a physiological saline solution. FIG. 4A illustrates how a syringe 58 can be used for injecting a solution of beads 64 in such a fluid into a tumor 66 disposed inside a patient's body, as shown in a partial cross section view 50. A needle 60 that is connected to syringe 58 is inserted through an epidermal layer 52 and dermal layer 54 into tumor 66. Dash lines 62 illustrate previous injection sites where beads 64 have been injected into tumor 66. Once beads 64 are thus infused at spaced-apart locations within tumor 66, a light source that emits IR light is activated, causing the electrons within the glass phosphor material to recombine with holes in the material, emitting light that is used to administer the light therapy or PDT.

One of the primary advantages of using glass phosphor material for the phosphorescent shell in beads 64 (or in any of the other embodiments disclosed herein) is that the glass phosphor material is substantially less toxic than other types of phosphors or scintillators. The only significant disadvantage is the requirement to expose the glass phosphor material with IR (or other wavelength) light to cause the shorter wavelength light to be emitted.

Figure 11:
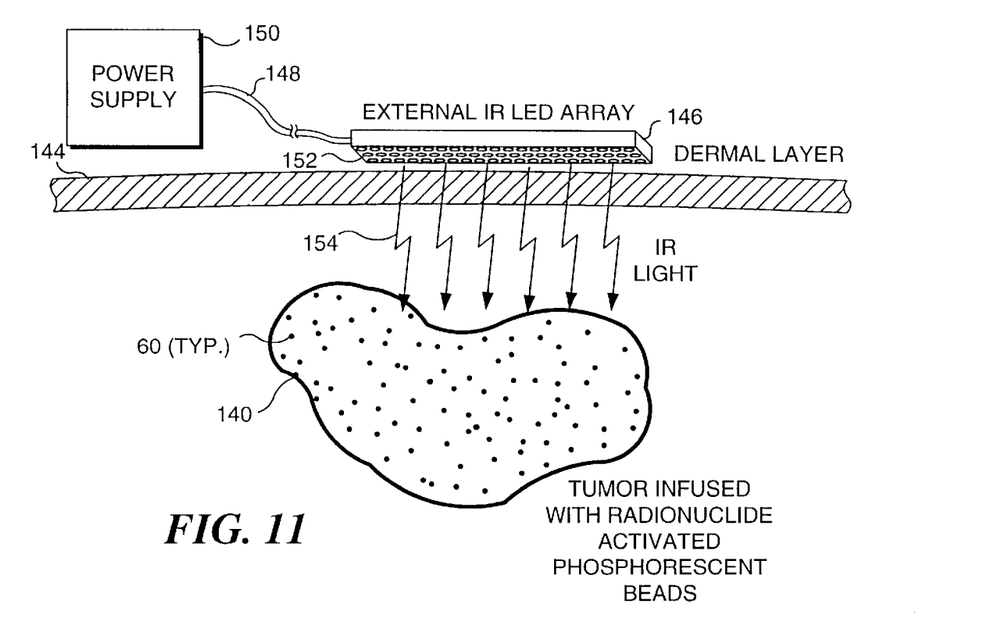
FIG. 11 is a schematic cross-sectional view of a tumor inside a patient's body, which has been infused with radionuclide activated phosphorescent particles and an external source of infrared (IR) light.
Figure 12:
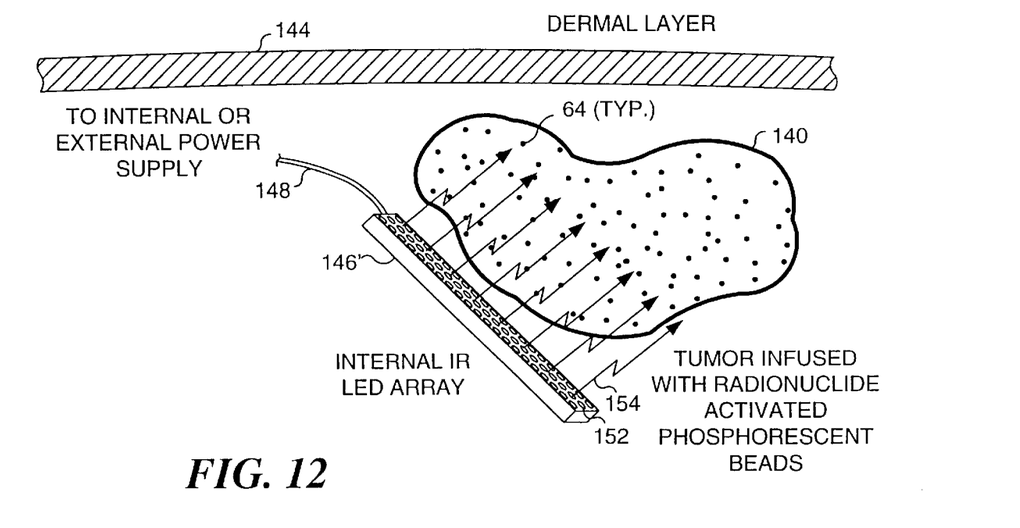
FIG. 12 is a schematic cross-sectional view of a tumor inside a patient's body, which has been infused with radionuclide activated phosphorescent particles and an internal source of IR light.
Figure 13:
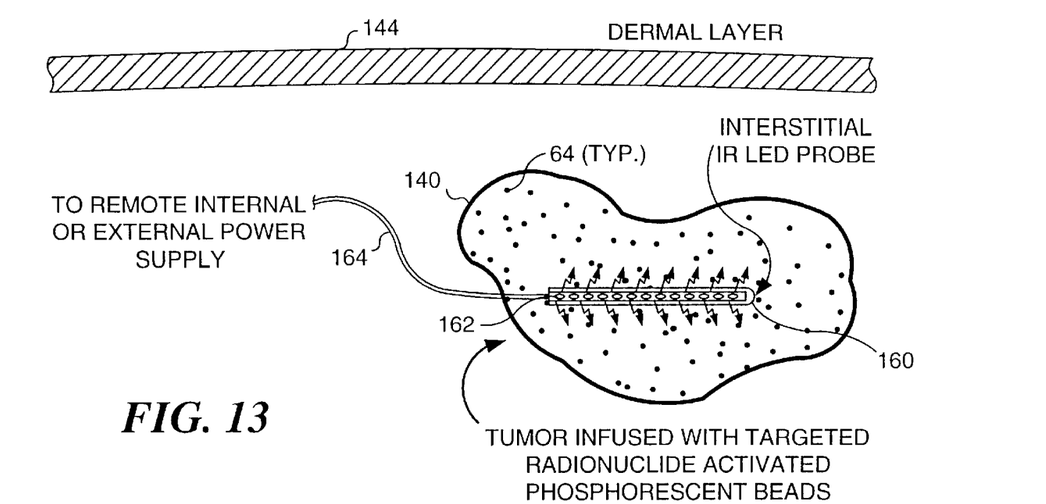
FIG. 13 is a schematic cross-sectional view of a tumor inside a patient's body, which has been infused with radionuclide activated phosphorescent particles and an interstitial probe that is a source of IR light.

Turning now to FIGS. 11–13, several examples are shown to illustrate how IR light can be applied. In FIG. 11, a tumor 140 has been infused with radionuclide activated phosphorescent beads 64. The beads can be infused either within a biocompatible fluid, or can be applied topically to the exterior surface of tumor 140. Tumor 140 lies within the patient's body, adjacent a dermal layer 144. Outside the patient's body, a power supply 150 is coupled through a lead 148 to an external IR LED array 148. Array 148 comprises a plurality of IR LEDs 152 arranged in spaced-apart array. When energized by power supply 150, LEDs 152 emit IR light 154 that passes freely through the dermal layer and into tumor 140, activating particles 64 so that they emit light of the appropriate wave band to administer the light therapy or PDT, to destroy tumor 140.

In FIG. 12, an alternative arrangement is illustrated in which an internal IR LED array 146' is connected through lead 148 to an internal (or external) power supply (not shown). Internal IR LED array 146' is implanted so that it is disposed adjacent or proximate to tumor 140. Implanting the IR LED array may be necessary if tumor 140 is disposed in a location within the patient's body where the IR light cannot penetrate if applied externally.

FIG. 13 illustrates yet another technique for exposing beads 64 to IR light. In this approach, a probe 160 is disposed interstitially within tumor 140. Probe 160 includes a linear array 162 of the IR LEDs that are energized through a lead 164, which is coupled to a remote internal (or external) power supply (not shown). If disposed internally, the power supply mentioned in regard to FIGS. 12 and 13 can be energized using an external power source that is electromagnetically coupled to the internal power supply. A detailed description of apparatus suitable for providing such electromagnetic coupling is described in U.S. Pat. No. 5,715,837, which is assigned to the same assignee as the present invention.

Figure 6:
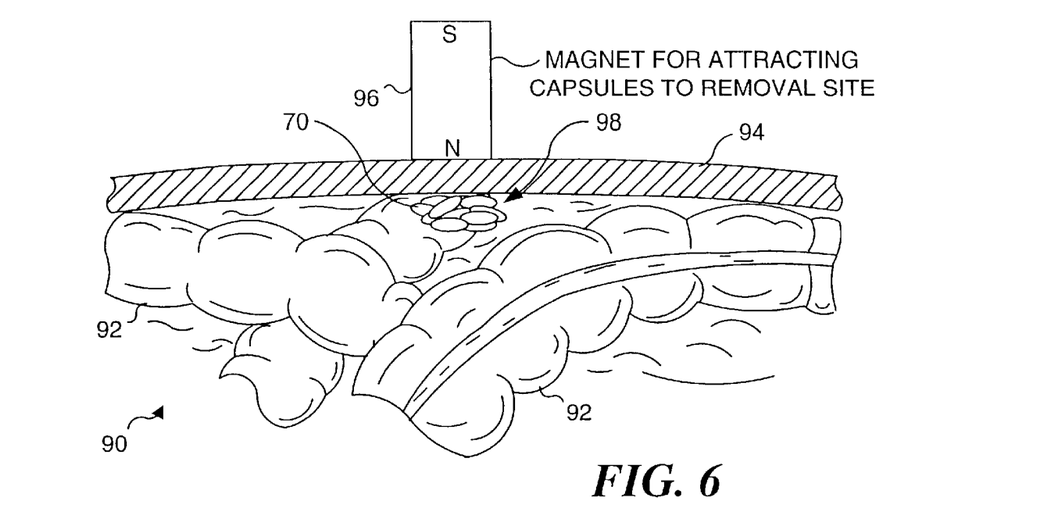
FIG. 6 is a cross-sectional view of a portion of a patient's abdomen, showing part of the colon/intestine and illustrating an external magnet that is used to attract the embodiment like that shown in FIGS. 5A and 5B.

A different type of capsule 70 is illustrated in FIGS. 5A and 5B. In capsule 70, a ferro-core 74 is included within a radionuclide core 72. Ferro-core 74 comprises any metal that is magnetically attracted by a magnetic field. Surrounding radionuclide core 72 is a phosphorescent shell 76. A biocompatible coating 78 completely surrounds phosphorescent shell 76, preventing it from coming into contact with tissue or fluids within the patient's body. As mentioned previously, biocompatible coating 78 is substantially optically transparent and comprises a polymer selected to absorb energetic particles that are emitted by radionuclide core 72, but which were not absorbed by the phosphorescent shell. The energetic particles emitted by the radionuclide core cause light to be emitted by phosphorescent shell 76, and the light passes through the biocompatible coating to provide the light therapy or PDT to a treatment site. Although the preceding function is generally identical to that of the embodiments already described, inclusion of ferro-core 74 enables capsules 70 to be attracted with a permanent magnet 96 to a removal site 98, as illustrated in FIG. 6. In this FIGURE, capsules 70 have been implanted within a patient's abdomen proximate a treatment site (not shown). At the conclusion of the light therapy or PDT, a permanent magnet 96 is applied externally to a dermal layer 94 at or around the treatment site, causing the capsules 70 to be drawn to removal site 98. Using permanent magnet 96, capsules 70 are thus collected at removal site 98 and be readily removed through a small incision in dermal layer 94 at the removal site, using suction, or other appropriate means. Using this technique, a minimally invasive procedure is employed that has little effect on a colon or bowel 92 within the abdomen.

Figure 7:
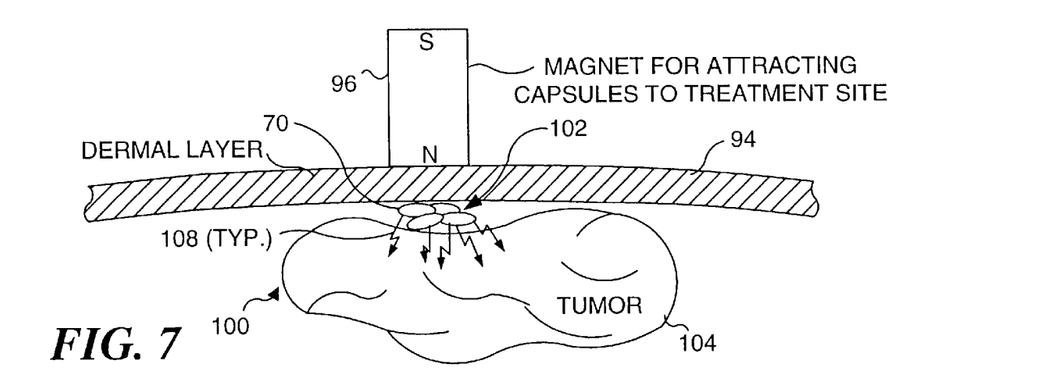
FIG. 7 is a cross-sectional view of a portion of a patient's body in which a tumor is disposed and illustrating an external magnet that is used to attract the embodiment shown in FIGS. 5A and 5B.

In FIG. 7, permanent magnet 96 is employed to attract capsules 70 disposed within the patient's body to a treatment site 102 adjacent a tumor 104. Capsules 70 then emit light 108 to provide light therapy or PDT to tumor 104. Magnet 96 can be left in place during the interval of the PDT, but in many instances, may be removed until after the PDT has been administered, since it is unlikely that capsules 70 will drift very far from the treatment site during the period of the treatment.

Figure 8:
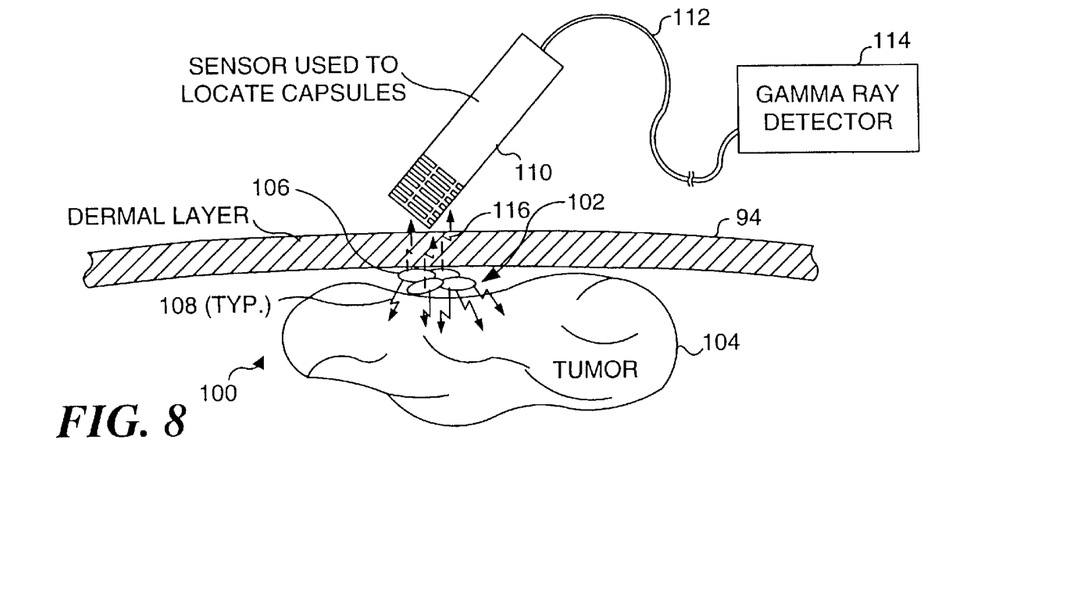
FIG. 8 is a cross-sectional view of a portion of a patient's body and illustrating a gamma ray detector for use in detecting a location in a tumor of an embodiment of the present invention that emits gamma rays.

If a very small amount of a gamma ray emitting substance is included within the radionuclide core, a capsule 106 can readily be located using a gamma ray sensor 110 that is coupled through a lead 112 to a gamma ray detector 114. Gamma ray sensor 110 is moved over the outer surface of dermal layer 94 until it picks up gamma rays 116 that are emitted from the radionuclide core of capsules 106. It is also contemplated that ultrasonic imaging and other techniques can be used for locating any of the embodiments of the present invention described herein.

Figure 9:
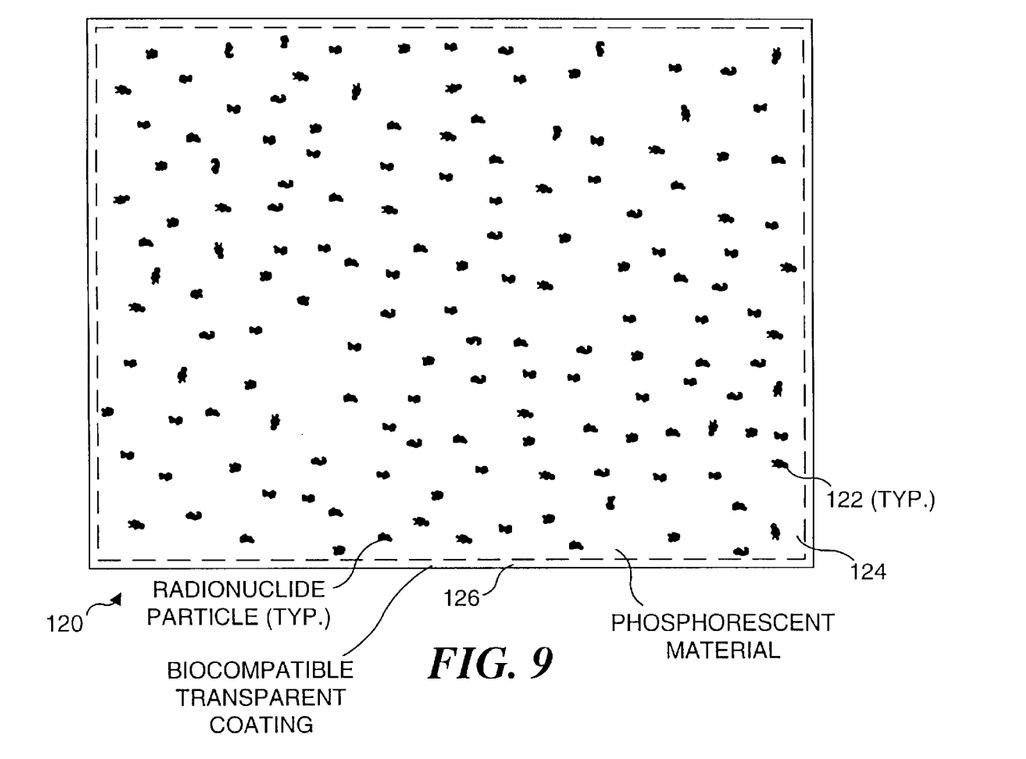
FIG. 9 is a plan view of a sheet like embodiment of the present invention, showing distributed radionuclide sources within the sheet.
Figure 10:
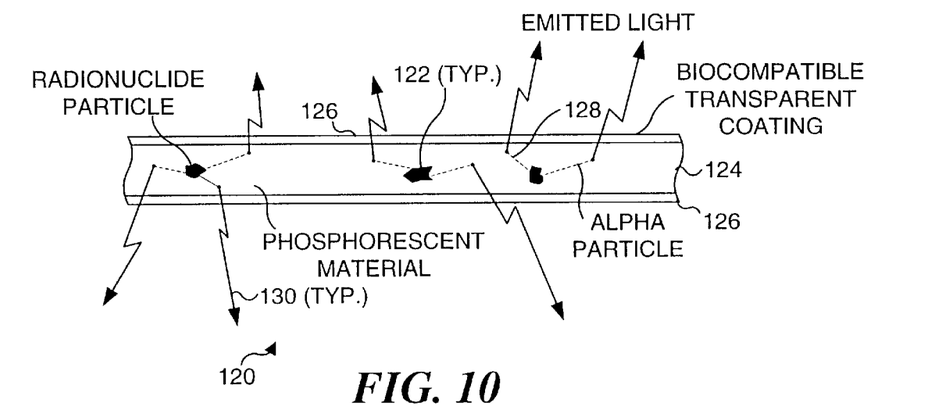
FIG. 10 illustrate a partial cross-sectional view of the sheet like embodiment of FIG. 9.

FIG. 9 illustrates a sheet 120 in which radionuclide particles 122 are distributed within an internal core 124 of phosphorescent material. Again, a biocompatible coating 126 encapsulates phosphorescent core 124 and radionuclide particles 122. The radionuclide particles emit alpha particles 128 (or other energetic particles) which are absorbed by the phosphorescent material, causing it to emit light through the surface of sheet 120. Although not shown, it is also contemplated that a reflective mirror layer can be used along one surface of phosphorescent material 124 to insure that the light is emitted through only one surface of sheet 120. In FIG. 10, light 130 passes through both surfaces of sheet 120.

Figure 14:
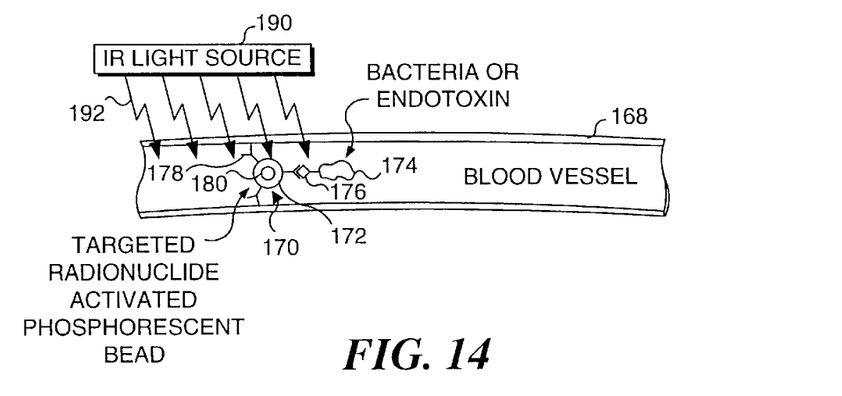
FIG. 14 is a cross-sectional view of a blood vessel illustrating a targeted radionuclide activated phosphorescent particle linked to a bacteria or endotoxin, and showing an IR light source.
Figure 15A:
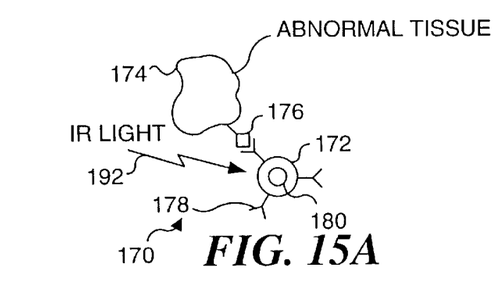
FIGS. 15A and 15B schematically illustrate a targeted radionuclide activated phosphorescent particle linked to abnormal tissue, respectively showing the energy level of the phosphorescent material being elevated by exposure to IR light, and the emission of shorter wavelength light from the phosphorescent material.
Figure 15B:
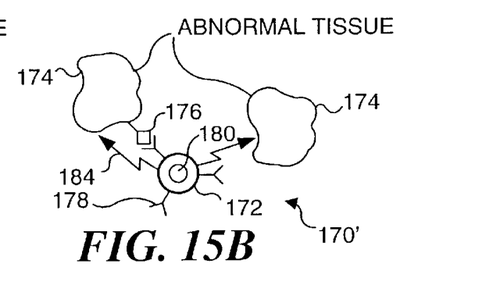

Rather than injecting beads 64 at a treatment site within a patient's body, it is also contemplated that targeted radionuclide activated phosphorescent beads 170 can be employed to selectively bind to abnormal tissue at one or more treatment sites in the patient's body. As illustrated in FIG. 14, the beads 170 are conveyed through a blood vessel 168 after having been infused into the vascular system at a different point. Beads 170 comprise a radionuclide core 180 surrounded by a glass phosphor material shell 172. A biocompatible coating surrounds the radionuclide core and glass phosphor shell. The biocompatible coating either comprises a material that selectively is targeted to link to abnormal cells such as a bacteria or endotoxin 174 or includes antibodies or other linking systems that selectively link to antigens 176 on the abnormal cells. Since the linking antibodies 178 or other linking paradigm that is coupled to or comprises the biocompatible coating does not selectively target normal cells, the beads freely pass through the circulatory system until they reach a treatment site at which the abnormal tissue for which they are targeted is disposed. At that point, the beads link to the abnormal tissue so that when light is emitted by the phosphorescent shell or glass phosphor material, it impacts upon the abnormal tissue to which the beads are linked. FIGS. 15A and 15B illustrate beads 170 linked to antigens 176 by antibodies 178 that are coupled to the biocompatible coating of the beads.

Since glass phosphor material has been used for the phosphorescent shell on beads 170, an IR light 192 is applied from an IR light source 190 (as shown in FIG. 14), causing beads 170 to emit light 184 that strikes abnormal tissue 174. In FIG. 15B, bead 170' has a darker outline, indicating that electrons produce by the ionizing radiation from radionuclide core 180 have been activated by the IR light, causing the glass phosphor material to emit shorter wavelength light 184 that impacts abnormal tissue 174. It should also be noted that phosphorescent material can be used for the shell of the beads infused in the body that does not include the glass phosphor material, and need not be exposed to IR light (or other light) before emitting light to administer the light therapy for PDT.

TABLE 1

| Radionuclide Core Isotopes | Type Of Particle Emitted | Half-Life | Scintillator or Phosphor | Wavelength of Emitted Light |
|---|---|---|---|---|
| Tritium | β | 12 yr. | $ZnWO_4$ | 480 nm |
| 212 Bi | α | 1 hr. | $Bi_4Ge_3O_{12}$ | 480 nm |
| 212 At | α | 7 hr. | CsI:Tl | 560 nm |
| 198 Au | β | 2.7 days | Anthracene | 434 nm |
| 32 P | β | 14 days | | |
| 222 Rn | α | 3.8 days | | |
| 90 Y | β | 2.6 days | | |
| 90 Sr | β | 28 years | | |

In regard to the radionuclide isotopes shown in Table 1, it should be noted that it is generally best to select a radionuclide material that has a half-life measured in months to ensure there is adequate time for shipping and to provide some shelf life for the construct in which the radionuclide material is included, before the construct is used in a patient. Once the light therapy has been administered to the treatment site by the construct for the required duration, it would be desirable for the radionuclide to stop emitting energetic particles as soon as possible to minimize risk of any adverse effects on the patient. Since it may be impossible to locate and remove all of the construct devices from the patient's body, there should be a minimal risk of any construct made in accord with the present invention remaining in the patient's body indefinitely. However, the radionuclide core should preferably be "dead" by the time the constructs are removed from the patient's body.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A construct for administering a light therapy to an internal treatment site within a patient's body, comprising:
   (a) a source of energetic nuclear particles;
   (b) a substance that absorbs the energetic nuclear particles and in response thereto, emits light having a characteristic wave band, said substance being disposed proximate to the source of energetic nuclear particles; and
   (c) a substantially optically transparent, biocompatible envelope surrounding the source of energetic nuclear particles and the substance, said light passing through the envelope to provide the light therapy to the treatment site.

2. The construct of claim 1, wherein the source of energetic nuclear particles comprises a core that is at least partially surrounded by a shell of the substance that emits light, said envelope enclosing the shell and the core to prevent direct contact between the patient's body and either the source of the energetic particles or the substance.

3. The construct of claim 1, wherein the envelope comprises a material that absorbs at least some of the energetic nuclear particles that are not absorbed by the substance.

4. The construct of claim 1, wherein the envelope comprises a material that molecularly binds to a cell at the treatment site, linking the envelope, the source of energetic particles, and the substance to said cell so that the light emitted by the substance is absorbed by said cell.

5. The construct of claim 1, further comprising a magnetically attracted component so that the construct is magnetically attracted to the treatment site with a magnetic field.

6. The construct of claim 5, wherein the magnetically attracted component enables the construct to be magnetically attracted to a removal site with a magnetic field after the light therapy has been administered, thereby facilitating removal of the construct from the patient's body at the removal site.

7. The construct of claim 1, wherein the source of the energetic nuclear particles is formed into a sheet having a thickness substantially less than either a width or a length of the sheet.

8. The construct of claim 1, wherein the source of the energetic nuclear particles is formed into a generally elongate configuration.

9. The construct of claim 1, wherein the substance comprises a phosphorescent compound having electrons that are excited to higher energy states by absorption of the energetic nuclear particles emitted from the source, said electrons then emitting the light as they drop to lower energy states.

10. The construct of claim 9, wherein the phosphorescent compound comprises a sulfide molecule.

11. The construct of claim 1, wherein the substance comprises a glass phosphor doped with metal ions that exhibits a stimulated luminescence.

12. The construct of claim 1, wherein the energetic nuclear particles comprise one of alpha particles and beta particles.

13. The construct of claim 1, wherein the envelope is substantially spherical.

14. The construct of claim 1, wherein the envelope has a maximum dimension in a range between $10^{-4}$ mm and 10 mm.

15. The construct of claim 1, wherein the source of energetic nuclear particles further comprises an emitter of gamma radiation, said gamma radiation facilitating detection and location of the construct within a patient's body, thereby enabling the construct to be removed after the light therapy has been administered.

16. The construct of claim 1, wherein the source of the energetic nuclear particles is selected to have a specific half-life based upon an expected required duration of the light therapy so as to minimize a risk of exposing the patient's body to the energetic nuclear particles after the light therapy has been completed.

17. The construct of claim 1, wherein the source of the energetic particles comprises one or more isotopes of an element selected from the group consisting of hydrogen, gold, phosphorus, radon, yttrium, and strontium.

18. The construct of claim 1, wherein the construct is suspended within a biologically compatible liquid for delivery to the treatment site.

19. A method for administering a light therapy to an internal treatment site within a patient's body, comprising the steps of:
   (a) providing a source of energetic nuclear particles;
   (b) placing a substance that absorbs the energetic nuclear particles and in response thereto emits light having a characteristic wave band, proximate the source;
   (c) hermetically enclosing the source and the substance that emits light within a substantially optically transparent and biocompatible envelope; and
   (d) positioning the envelope adjacent to the treatment site within the patient's body so that the light emitted by the substance passes through the envelope and is incident on the treatment site.

20. The method of claim 19, further comprising the step of administering a photoreactive agent characterized by being preferentially absorbed by abnormal tissue at the treatment site and having an absorption wave band generally corresponding to the characteristic wave band of the light emitted by the substance, said light destroying the abnormal tissue that has preferentially absorbed the photoreactive agent.

21. The method of claim 19, wherein the step of positioning the envelope comprises the steps of:

(a) disposing a component that is magnetically attracted within the envelope; and (b) applying a magnetic field to the treatment site to move the component that is magnetically attracted, the source, and the substance to the treatment site.

22. The method of claim 19, further comprising the steps of:

(a) providing a component that is magnetically attracted within the envelope;

(b) employing a magnetic field to attract the construct with the component to a removal site; and (c) removing the source and the substance from the patient's body at the removal site, after the light therapy has been administered.

23. The method of claim 19, wherein the step of positioning the envelope comprises the step of injecting a construct comprising the envelope, the source, and the substance into a cavity disposed within the patient's body.

24. The method of claim 23, further comprising the step of suspending the construct within a biocompatible fluid for injection into the cavity.

25. The method of claim 23, wherein the construct is not absorbable into the body through walls of an organ, a peritoneum membrane, or a pleura membrane.

26. The method of claim 19, further comprising the step of molecularly binding the envelope to abnormal cells at the treatment site while the light therapy is being administered to the abnormal cells.

27. The method of claim 23, further comprising the step of detecting a location of the construct within the patient's body by sensing the energetic nuclear particles emitted from the source.

28. The method of claim 27, further comprising the step of removing the construct from the patient's body after its location has been identified and after the light therapy has been administered.

29. The method of claim 19, further comprising the step of forming the source into a sheet having a thickness substantially less than either a width or a length of the sheet.

30. The method of claim 19, further comprising the step of forming the source into a generally elongate configuration.

31. The method of claim 19, wherein the substance comprises a phosphorescent compound in which valence electrons are excited to higher energy states by absorption of the energetic nuclear particles emitted from the source, said valence electrons then emitting the light as they drop to lower energy states.

32. The method of claim 31, wherein the phosphorescent compound comprises a sulfide molecule.

33. The method of claim 19, wherein the substance comprises a glass phosphor fused with metal ions that exhibits stimulated luminescence, said glass phosphor fused with metal ions trapping electrons when exposed to the energetic nuclear particles emitted from the source.

34. The method of claim 33, further comprising the step of causing the electrons to be released to emit the light within a first wave band by exposing the glass phosphor fused with metal ions to a light within a second wave band.

35. The method of claim 19, wherein the energetic nuclear particles comprise one of alpha particles and beta particles.

36. The method of claim 19, wherein a half-life of the source of the energetic nuclear particles is selected as a function of a duration of the light therapy so as to minimize a risk of exposing the patient's body to the energetic nuclear particles after the light therapy has been completed.

37. The method of claim 19, wherein the source of the energetic particles comprises one or more isotopes selected from the group consisting of hydrogen, gold, phosphorus, radon, yttrium, bismuth, astatine, and strontium.

38. The method of claim 19, wherein the envelope is formed in a generally spherical configuration.

* * * * *